United States Patent [19]

Holzer

[11] Patent Number: 4,718,430
[45] Date of Patent: Jan. 12, 1988

[54] PROCEDURE AND DEVICE FOR THE ADMINISTERING OF INSULIN OR SIMILAR LONG-TERM MEDICAMENTS

[76] Inventor: Walter Holzer, Drosteweg 19, Meersburg, Fed. Rep. of Germany, 7758

[21] Appl. No.: 778,124

[22] Filed: Sep. 20, 1985

[30] Foreign Application Priority Data

Sep. 22, 1984 [DE] Fed. Rep. of Germany ....... 3434832
Jan. 18, 1985 [DE] Fed. Rep. of Germany ....... 3501534

[51] Int. Cl.$^4$ .......................... A61B 5/00; A61M 1/03
[52] U.S. Cl. ...................................... 128/632; 604/50; 604/67; 604/890.1
[58] Field of Search .................. 604/28, 66, 50, 65, 604/67, 890, 892; 128/632–635

[56] References Cited

U.S. PATENT DOCUMENTS

| | | | |
|---|---|---|---|
| 3,786,813 | 1/1974 | Michaels | 604/892 |
| 3,788,322 | 1/1974 | Michaels | 604/890 |
| 3,797,492 | 3/1974 | Place | 604/890 |
| 3,840,009 | 10/1974 | Michaels et al. | 604/892 |
| 4,055,175 | 10/1977 | Clemens et al. | 604/66 |
| 4,073,292 | 2/1978 | Edelman | 604/66 |
| 4,151,845 | 5/1979 | Clemens | 604/66 |
| 4,237,881 | 12/1980 | Beigler et al. | 604/65 X |
| 4,445,885 | 5/1984 | Kifune | 604/66 X |
| 4,538,616 | 9/1985 | Rogoff | 604/66 X |

Primary Examiner—William E. Kamm
Assistant Examiner—Angela D. Sykes
Attorney, Agent, or Firm—Boniard I. Brown

[57] ABSTRACT

A procedure for the administration of insulin or similar long-term medicaments utilizing an elastic element, for example a membrane dividing a reservoir into two chambers, one of which holds the medicament and the other containing a temperature-dependent vapour pressure and the remaining liquid propellant gas. By means of the membrane, the medicament, permanently pressurized by the propellant gas, is injected into the body through an outlet opening. The invention seeks to achieve differing ratios of medicament dosage by providing for the external raising of the temperature of the propellant and thereby the pressure of the gas, and thus increasing the injected quantity at required time intervals. It is preferred that the dosage be dependent on the level of blood sugar in the body.

16 Claims, 7 Drawing Figures

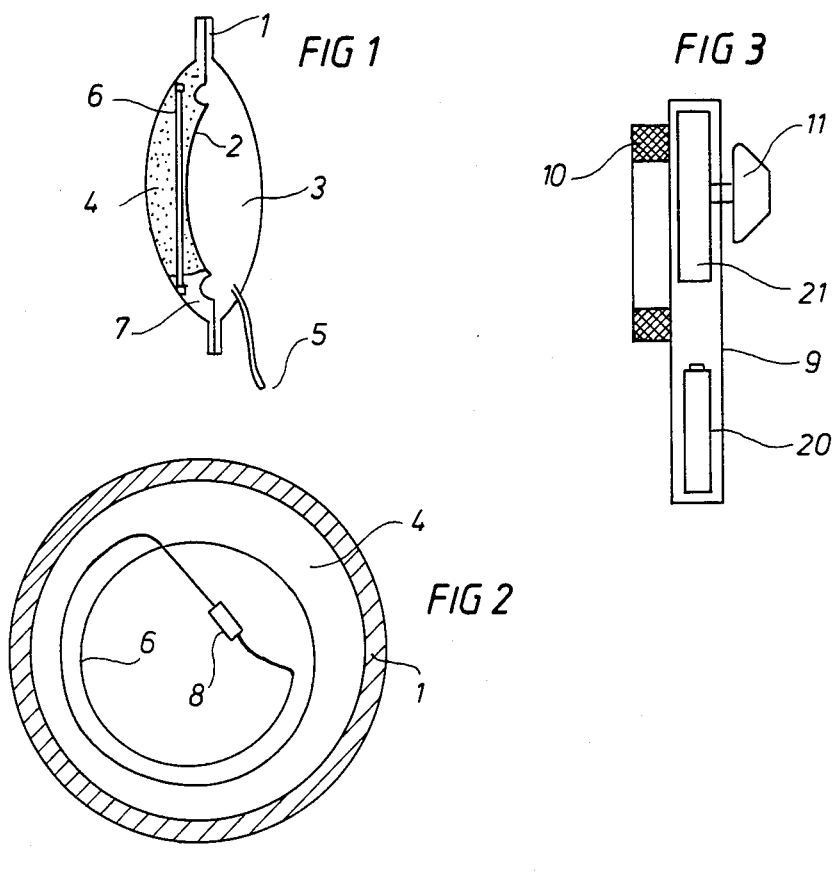
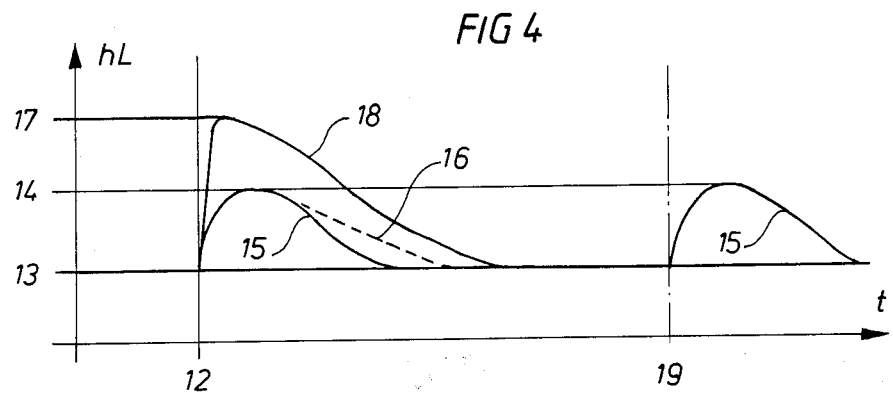

PROCEDURE AND DEVICE FOR THE ADMINISTERING OF INSULIN OR SIMILAR LONG-TERM MEDICAMENTS

BACKGROUND OF THE INVENTION

The invention concerns a procedure for the administration of insulin or other long-term medicaments as stated in the introductory description. A procedure of that kind is, for instance, known with the object of AT-PS No. 367,292. Devices of similar function are for example, also known under U.S. Pat. Nos. 3,840,009, 3,786,813 or 3,788,322 and 3,797,492.

All known systems have the disadvantage that the pressure of the gas-filled chamber of the reservoir is dependent on the body temperature of the long-term patient. The disadvantage is therefore that only predetermined quantities of medicament can be administered, extra dosages as required are not possible.

BRIEF SUMMARY OF THE INVENTION

The invention therefore is tasked with the further development of the known devices, as above, in such a way that extra dosage as required is made possible.

To meet this requirement, the invention is characterized in that the temperature of the propellant gas, and thereby the pressure and thus the increased dosage at the required time intervals, is increased externally. It is hereby preferred that inductive or capacitive coupling is used as a means of temperature increase.

To co-ordinate the rise in temperature and thereby the extra dosage requirements, a measured energy impulse is recommended. This extra dosage requirement can be achieved either by changing its intensity through an amplitude change, or a combination of both methods.

The simplicity of this procedure is particularly apparent when the object of the invention to carry out the procedure is considered: It is proposed that a short-circuited induction coil is located in the heat-influenced area of the propellant gas, that is the remaining ,as yet unevaporated liquid gas. This location enables, in the simplest fashion, the external energy impulses to raise the temperature of the system.

To avoid unintentional increases in temperature and thereby a possible overdose, a temperature-limiting device e.g. a thermistor is provided as a constructional part. Such a device contains a temperature-dependent resistor the characteristics of which can be set so that at a specific upper temperature the resistance increases dramatically thus shutting off further current flow. Such parts have been fitted to many industrial products over a period of years, being absolutley reliable and maintenance-free.

The external influencing of the dosage is achieved, after the terms of the invention, by a control device which contains a primary coil which can be coupled to the induction coil. If this primary coil is energized by an alternating current and brought into the area of the induction coil, a secondary current is induced after the fashion of a transformer.

To ensure that the dosage is administered as required, it is further proposed to fit adjustable and/or programmable control elements in the control device which influence either the length or the amplitude of the induced current. Naturally the length of the amplitude can be simultaneously altered.

In a particularly preferred version of the invention it is proposed that the change in temperature of the propellant gas is controlled dependent on the level of blood sugar of the patient. The blood sugar level is to be recorded by adequate known methods. An example is described in the magazine "Medical and Biological Engineering and Computing" September 1984 edition, pages 385 to 397. Such a type of implanted probe to record the blood sugar level is particularly suitable for use with the submitted invention.

Together with the direct recording of the blood sugar level by such a probe, indirect procedures for the establishment of blood sugar levels can also be used, for example the onset of specific physiological symptoms (sweating,pulse rate, skin temperature), as indications of a dangerously low blood sugar level.

It is proposed that with the self-monitoring and progressive recording of blood sugar levels the specific required dosage of the long term medicament is automatically administered to the patient commensurate with the basic idea of the invention.

In the submitted invention, two radically differing layouts for the administering of a long-term medicament are proposed. A first layout is provided in that purely the secondary circuit together with the reservoir, which is divided into two chambers as already mentioned, is implanted into the body, in which the secondary circuit is inductive controlled externally from a primary circuit fitted outside the body of the patient. This device has the advantage that because of the low number of construction parts it takes up very little space and is thus easy and simple to implant.

In a second type of layout of the submitted invention provision is made for the secondary circuit to be autonomous, that is, it is equipped with its own energy source, thus dispersing with the inductive coupling for energy supply mentioned previously. In this autonomous secondary circuit, then, only one control element is designed into which is built, as an example, a microprocessor. The daily basic requirements are programmed into this microprocessor and this regulating facility correspondingly controls the heating element which, corresponding to the input of the regulating facility, raises or lowers the temperature of the propellant gas.

For extra requirements of the long-term medicament, the microprocessor is externally controlled. The control is achieved in conjunction with the blood sugar monitoring probe which can control the regulating facility in the secondary circuit either with or without wiring.

Both foregoing layouts are differentiated from each other in that in the case of the first layout a passive secondary circuit is available in which the necessary energy must be supplied either by inductive or capacitive means, whereas in the second layout example the secondary circuit is energy-independent and therefore an inductive energy supply can be dispensed with. The control commands for the regulating facility in the secondary circuit can, therefore be supplied by inductive or capacitive means or by wiring.

A further layout form of the submitted invention distinguishes itself by its economic dosage of the discharged Insulin. In the previously mentioned layout forms, the medicament is injected into the body through a capillary tube, which tube is preferred to consist of drawn glass piping and can have a length of up to 10 m. To save space, this tube is wound spirally around the reservoir.

The following described layout forms stand out in that such a capillary tube can be dispersed with as another possibility for measured doses of the medicament (e.g. insulin) is proposed.

In this layout example a divided middle chamber is fitted between the liquid gas propellant chamber and the insulin-holding chamber to measure out the insulin dosage from the outlet aperture, which is filled with a low viscosity fluid (e.g. water). Both chambers are separated by a rigid partition in which are fitted a non-return valve and a choke bore. By switching between either of these two chambers an exact dosage of the Insulin discharged into the tissue is possible, in that the discharge rate is determined by the size of the choke bore. The chamber containing the medicament (e.g. insulin) can be externally refilled using a hollow needle whereby the needle penetrates an elastic plug to enable the chamber to be refilled. By this action, both membranes of this layout are again deformed and a non-return valve is provided in the partition to guarantee a quick deformation which also guarantees a quick return flow of water from one chamber to the other.

The disclosure of the submitted invention arises not only from the object of the single patent claims but also from a combination of the single patent claims one with another. All of the statements and features disclosed in the documents, particularly the construction detailed in the illustrations are claimed as essential to the invention, in so far as they, either singly or in combination, are new relative to the current state of the art.

In the following, the invention is further explained by means of merely one form of layout. Further features and advantages arise from the illustrations and their descriptions which are deemed to be essential to the invention.

BRIEF DESCRIPTION OF THE DRAWINGS

FIG. 1: Schematic section of dosage equipment after the style of the invention.

FIG. 2: Vertical section through liquid gas propellant chamber of the dosage equipment.

FIG. 3: Schematic side-view of the control device to be carried outside the body.

FIG. 4: Differing dosage/time graphs.

Figure 5:
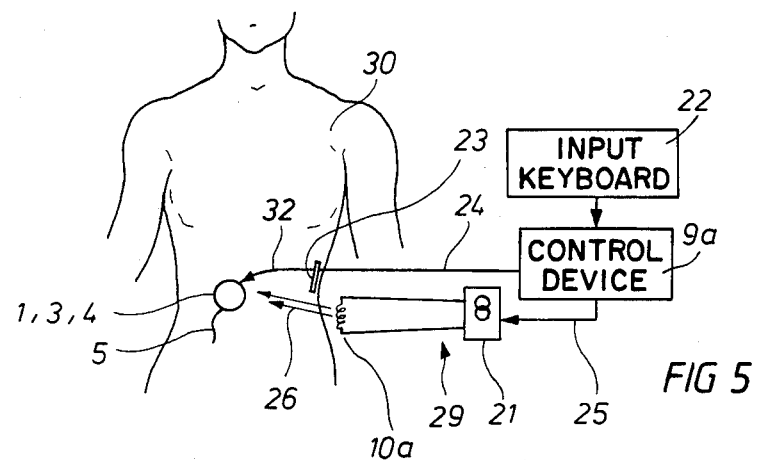
FIG. 5: Schematic layout of a sugar-dependent control of the dosage equipment.

DESCRIPTION OF THE PREFERRED EMBODIMENT;

The reservoir 1 is divided by membrane 2 into two chambers 3 and 4. Chamber 3 contains the medicament, e.g. insulin which is injected into a vein or tissue through outlet aperture 5, in this case shown as a capillary tube.

Propellant gas together with its liquid gas 7 is contained in chamber 4 which is hermetically sealed and seperated from the medicament by membrane 2. The pressure of the propellant gas is only determined by the environmental body temperature of the patient. In the case of implanted equipment, a closely fitted and reliable thermal coupling is assured.

The pressure of the propellant gas continually presurizes the medicament in chamber 3 by means of the membrane 2 thereby determining the quantity of the fluid discharging through the outlet aperture 5. Although this action continually reduces the volume of chamber 3 the pressure does not change as, simultaneously, a specific volume of liquid gas evaporates to correspondingly increase the volume of the propellant gas. The body temperature thus maintains the system in a static condition relative to the gas pressure.

The possibility to increase the dosage is, achieved in this invention by the raising of the gas pressure.This is achieved by the induction coil 6 shown in FIGS. 1 and 2, which is located directly in the region of the propellant gas/liquid gas 7.

It is essential that such an induction coil 6 can be energized in the simplest way from an external source so that in its short-circuited condition it functions as a heating coil. In this fashion the temperature of the gas and thereby the gas pressure and subsequently the injected fluid quantity can be increased.

For safety reasons, it must be assured that an overdose, caused by incorrect handling or malfunction, cannot occur. This is achieved by the thermistor 8 which is fitted into the induction coil 6 circuit. Naturally other solutions are possible e.g. thermostatic contact which breaks the circuit at a specific predetermined temperature.

The energy is advantageously supplied by a portable control device 9 which contains a primary coil 10 as in a transformer. This primary coil 10 can be either connected to the mains circuit, or, to make it independent of mains supply, battery 20 powered via an alternator 21. This makes it possible to work with the higher frequency of alternating current to achieve a better coupling with the induction coil.

FIG. 3 also shows as an example, a form of layout of the programme controller 11 which permits adjustment of the duration and/or amplitude of the induced voltage. Depending on the required dosage one or the other can be more economic.

FIG. 4 shows, in a quantity/time graph the respective induced Insulin quantities in nanoliters over a time-base "t". A constant quantity 13 is injected without interference if, at time-point 12 , e.g. 12.00 hrs., an extra dose is required, the dosage can be increased to that shown at 14 . Depending on the layout of the dosage device, a longer or shorter cooling time results which again corresponds to regular dosage curves 15 or 16.

A greater amplitude or induced voltage, or longer duration corresponds to an increased heating effect and therefore to an extra dosage quantity 17 as shown in dosage curve 18.

A corresponding course of extra dosage is also possible as time-point 19 e.g. 19.00 hrs. as shown in FIG. 4. Such an extra dosage could not only be administered by hand, but also by the layout of the invented dosage device and the control device, A sequence programmed by a doctor for permanently installed control devices, is provided for.

The specified layout examples are in no way to be seen as a restriction. The references to the numerous variations by the alteration of the single parameters permit an exact adaptation to the respective given requirements.

The following examples are mentioned:

Adaptation of the coil windings of the primary coil 10 and induction coil 6.

Regulation of the duration and/or amptitude.

Sizing of the heat transfer from propellant gas chamber 4 to the surrounding tissue.

Limiting of the maximum heat temperature and other parameters.

In FIG. 5, a further form of layout of the dosage device according to the invention is shown. The dosage device is implanted in body 30 and, to record the level of blood sugar, a sensor 23 is provided which is connected to the control device 9a by wiring 24. The control device can be permanently programmed, or, in a further form of layout changes to the parameters can be made by use of the input keyboard 22.

The alternator 21 is controlled, through the wiring 25 by the control device 9a which controls, as required, the amplitude or impulse. The alternator 21 creates, together with the primary coil 10a, the primary circuit 29 which is coupled to the secondary circuit 6, 8 in the dosage device by the inductive coupling 26.

As described, a self-monitoring adjustment of the dosage of long-term medicaments depending on the blood sugar level in the body 30 is given.

Figure 6:
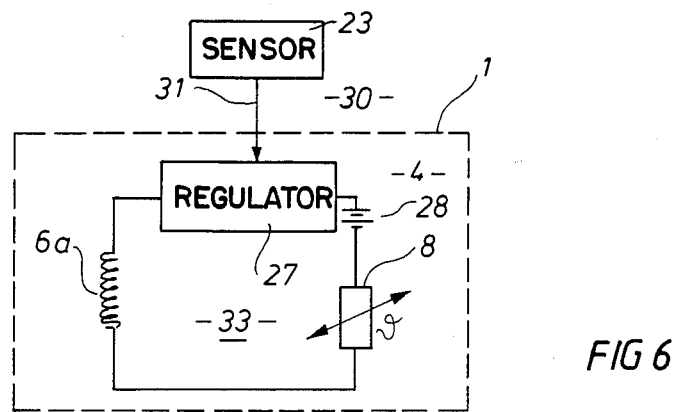
FIG. 6: Schematic circuit diagram of an energy-independent secondary circuit.

In FIG. 6, a further form of layout is illustrated which shows an energy-independent secondary circuit, which is a part of the body-implanted dosage device. The induction coil is no longer required, rather the coil used in the short-circuited circuit forms the heat generator 6a, which together with the regulator 27 a battery 28 and the thermistor 8 is a part of the secondary circuit.

The regulator 27 is controllable outside the body, with or without wiring by a suitable sensor 23, whereby this sensor again records the level of the blood sugar in the body. In this fashion an intercorporal or extracorporal programming of the regulator 27 through the blood sugar recording sensor 23 is possible. As specified, the wiring 31 can be formed as an inductive coupling or as an electrical conductor.

FIG. 5 illustrates a further variant of a form of layout using the connection 32 between the sugar probe 2 and the dosage device 1, 3, 4. In this variant the wiring 24 to the control device 9a is dispensed with. The sugar probe 23 influences the regulator 27 in heating circuit 6, 8 (FIG. 4) in such a fashion that at all times only the physiologically efficient and necessary quantities of the long-term medicament is released into the body 30, even if, externally, from the primary circuit 29 and control device 9a the administering of a larger quantity of medicament is called for. This internal control creates a self-monitoring limitation of the dosage of the long-term medicament to a physiologically safe level.

In FIG. 6 yet a further layout variant is possible in that inductive energy e.g. through the inductive coupling 26 (FIG. 5) is transmitted to the secondary circuit 33 from outside the body 30 either to recharge the battery 28 or to programme the control device 27 without contact.

Figure 7:
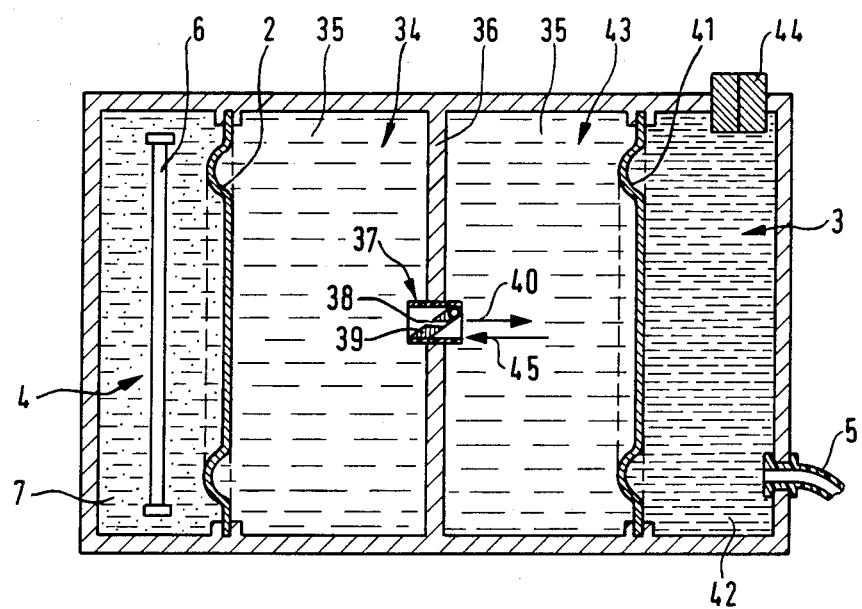
FIG. 7: Schematic section of a further form of layout.

In the layout example in FIG. 7, a middle chamber consisting of two chambers 34, 43 is fitted in between chamber 4 containing the liquid gas propellant 9 and chamber 3 containing Insulin. This middle chamber serves as a dosage device between chambers 3 and 4. Both chambers 35 and 43 are preferred filled with a low-viscosity fluid such as water. The left limit of the chamber 35 is formed by the flexible membrane 2 while the right limit is formed by a rigid, non-deflecting partition 36. Analogously, the left limit of the right hand chamber 43 is formed by the rigid partition 36 and the right hand limit of this chamber 43 is formed by a further flexible membrane 41 which is essentially of the same construction as membrane 2 and performs the same function. In the partition 36 a non-return valve 37 is fitted, which in the illustrated layout example is shown in schematic form as a valve flap 39, whereby the non-return valve 37 is closed off in arrow direction 40 for all fluid flow, but allowing fluid transfer from chamber 43 to chamber 34. Further, a choke bore 38 is provided in the partition 36 which is shown in the illustrated example layout to be located in the valve flap 39 for the sake of simplicity. This choke bore could, however, be located away from the valve flap 39, in the rigid partition 36.

On the other side of the membrane 41 the chamber 3 containing the medicament e.g. Insulin 42 is located, in which is the outlet aperture 5 through which the medicament is injected into the body tissue.

The propellant gas and the liquid propellant gas continually pressurize membrane 2 under the influence of the body temperature resulting in a constant injection of the medicament into the body tissue. To achieve an adjustment of the quantity of the injected medicament dependent on other physiological parameters, a temperature increase of between 10° and 20° Celsius in chamber 4 is enough to create a sufficient vapour pressure increase of the liquid propellant gas 7. As soon as the induction coil 6 in chamber 4 heats up the vapour pressure of the liquid propellant gas 7 increases and acts on the fluid 35 in chamber 34 through the self-deflecting membrane 2. This fluid 35 is then transferred through the choke bore 38 in the direction of arrow 40 into chamber 43 thus expanding the volume of this chamber thus deflecting the membrane 41 outwards and forcing the insulin 42 in chamber 3 out of the outlet aperture 5. Depending on the type, gauge and profiling of the choke bore 38, therefore, an exactly defined precise quantity of insulin 42 is discharged from chamber 3 through the outlet aperture 5. It is therefore unnecessary to fit a further restrictor in the outlet aperture. A similar restrictor was the previously mentioned capillary tube.

To refill the chamber 3 with medicament e.g. insulin 42 a hollow needle is introduced into an elastic plug 44 through the body tissue. This action deflects the membrane 41 in the opposite direction to that previously described and the previously mentioned non-return valve 37 provided in the partition 36 permits a rapid return deflection of membranes 41 and 42, so that the fluid 35 contained in chamber 43 flows rapidly through the open non-return valve 37 into chamber 34, which simultaneously deflects membrane 2. Subsequent to refilling, the equipment is available for a new service cycle.

The inventor claimed is:

1. A method for the administration of a long-term medicament, such as insulin, to the body of a person, comprising:
providing a dosage device having two chambers separated by an elastic membrane,
providing a quantity of the medicament in one of said chambers and providing a quantity of liquid propellant in the other chamber, said propellant having a temperature-dependent vapour pressure to maintain pressure on the medicament substantially continuously to inject medicament into the body via an outlet from the medicament chamber,
determining the need of the body for the medicament by sensing a blood component at certain times, and
varying the temperature of the propellant to vary its vapour pressure in accordance with said determination of need for the medicament at said certain times to control the quantity of medicament injected into the body at said certain times.

2. A method according to claim 1, wherein:
said medicament is insulin,
the determination of the need for the insulin is by sensing the blood sugar level in the body at the certain times, and
the propellant gas temperature is varied in accordance with the sensed level of blood sugar in the body.

3. A method according to claim 2, and further including the steps of:
implanting the dosage device in the body,
implanting a sensing device in the body to sense the blood sugar level at the certain times, and
providing a sugar level-responsive electronic regulator having a primary circuit outside the body and having a secondary circuit inside the body, said electronic regulator varying the electrical power supply to an electrical device at the dosage device to increase the propellant gas vapour pressure in accordance with the need of the body.

4. A method according to claim 2, and further including the steps of:
providing with the implanted dosage device a battery and a regulator, and
governing the electronic regulator by the output of the battery and sensing the blood sugar level of the body to control the power supply to said secondary circuit inside the body.

5. A method according to claim 2, and further including the step of:
providing an externally programmable digital control impulse device external of the body to control the medicament supply.

6. Apparatus for the administration of a long-term medicament, such as insulin, to the body of a person, comprising:
a dosage device implanted in the body and comprising a reservoir having two chambers separated by an elastic membrane,
one of said chambers containing the medicament and the other chamber containing a liquid propellant having a temperature-dependent vapour pressure to substantially continuously maintain pressure on the medicament via said membrane,
said chamber containing the medicament having an outlet in communication with the body,
means for determining at certain times the need of the body for the medicament by sensing a blood component of said person,
an electrical means at the dosage device for altering the temperature of the propellant to alter its vapour pressure to exert altered pressure via the elastic membrane to control the amount of medicament discharged through the outlet in accordance with the electrical power supplied to the device, and
means for controlling the electrical power supplied to said electrical device to govern the quantity of medicament dispensed at said certain times.

7. Apparatus according to claim 6, wherein:
said electrical device comprises a short-circuited induction coil comprising a secondary circuit, and
the apparatus includes a primary circuit outside the body to energize the secondary circuit.

8. Apparatus according to claim 7, and further including:
a temperature-limiting thermistor in said secondary circuit.

9. Apparatus according to claim 7, wherein:
the medicament is insulin,
said means for determining the need for the medicament comprises a sensor implanted in the body to sense the blood sugar level of the body, and
a control device outside the body governed by said sensor and controlled by an alternating current-supply primary circuit, a primary coil of the control device controlling the body-implanted secondary circuit by an inductive coupling.

10. Apparatus according to claim 9, and further including:
a battery and a regulator in said secondary circuit and controlled by said blood sugar level sensor implanted in the body.

11. Apparatus according to claim 9, and further including:
a central chamber defined between the chamber containing the medicament and the chamber containing the propellant gas, said central chamber being divided into two chambers by a rigid partition on which partition are mounted a one way valve and a choke bore, said central chamber being filled with low viscosity fluid.

12. Apparatus according to claim 7, and further including:
a battery and a regulator in said secondary circuit and controlled by said means for determining medicament need.

13. Apparatus according to claim 7, and further including:
a central chamber defined between the chamber containing the medicament and the chamber containing the propellant gas, said central chamber being divided into two chambers by a rigid partition on which partition are mounted a one way valve and a choke bore, said central chamber being filled with low viscosity fluid.

14. Apparatus according to claim 6, wherein:
the medicament is insulin,
said means for determining the need for the medicament comprises a sensor implanted in the body to sense the blood sugar level of the body, and
a control device outside the body governed by said sensor and controlled by an alternating current-supply primary circuit.

15. Apparatus according to claim 14, and further including:
a battery and a regulator in said secondary circuit and controlled by said blood sugar level sensor implanted in the body.

16. Apparatus according to claim 14, and further including:
a central chamber defined between the chamber containing the medicament and the chamber containing the propellant gas, said central chamber being divided into two chambers by a rigid partition on which partition are mounted a one way valve and a choke bore, said central chamber being filled with low viscosity fluid.

* * * * *